United States Patent
Mawer

(10) Patent No.: US 7,526,970 B2
(45) Date of Patent: May 5, 2009

(54) MILLIMETRE-WAVE DETECTION DEVICE FOR DISCRIMINATING BETWEEN DIFFERENT MATERIALS

(75) Inventor: William Richard Mawer, Boonton Township, NJ (US)

(73) Assignee: Smiths Detection-Watford Limited, London (GB)

( * ) Notice: Subject to any disclaimer, the term of this patent is extended or adjusted under 35 U.S.C. 154(b) by 374 days.

(21) Appl. No.: 10/572,264

(22) PCT Filed: Sep. 13, 2004

(86) PCT No.: PCT/GB2004/003902

§ 371 (c)(1),
(2), (4) Date: Mar. 16, 2006

(87) PCT Pub. No.: WO2005/029053

PCT Pub. Date: Mar. 31, 2005

(65) Prior Publication Data

US 2007/0056396 A1      Mar. 15, 2007

(30) Foreign Application Priority Data

Sep. 17, 2003    (GB) .................... 0321754.4

(51) Int. Cl.
G01D 21/02     (2006.01)
G01N 33/00     (2006.01)
G01N 22/00     (2006.01)
G01N 33/22     (2006.01)
G01N 1/02      (2006.01)

(52) U.S. Cl. .............. 73/866; 73/31.05; 73/31.07; 73/864.33

(58) Field of Classification Search .......... 73/866, 73/864.33, 31.02–31.03, 31.05, 31.07; 250/336.1, 250/338.1, 338.5, 358.1; 324/637; 342/27, 342/179

See application file for complete search history.

(56) References Cited

U.S. PATENT DOCUMENTS 4,896,547 A  *  1/1990  Arney et al. ............. 73/863.81

(Continued)

FOREIGN PATENT DOCUMENTS

EP          0 447 158 A2      9/1991

(Continued)

OTHER PUBLICATIONS

Terrorism and Drug Trafficking: Technologies for Detecting Explosives and Narcotics, U. S. General Accounting Office (GAO) Report to Congressional Requesters, Sep. 1, 1996, URL:http://www.gao.gov/archive/1996/ns96252.pdf> retrieved on Nov. 5, 2004 (30 pgs.).

(Continued)

*Primary Examiner*—Thomas P Noland
(74) *Attorney, Agent, or Firm*—Foley & Lardner LLP

(57) ABSTRACT

A portal (1) has a millimetric wave imager (10, 11) arranged to detect articles concealed on the person. A pump (21) supplies jets of air through gas outlets (20) in the lower part of the portal (1), which are directed onto the feet of the person being screened. A second pump (25) pumps air with substances released by the jets via inlets (22) to an ion mobility spectrometer (24) arranged to detect the presence of explosives or narcotics. A screen (12) indicates the presence of any suspect article or substance on the person being screened.

8 Claims, 1 Drawing Sheet

U.S. PATENT DOCUMENTS 5,227,800 A 7/1993 Huguenin et al.
6,353,224 B1 * 3/2002 Sinclair et al. ........... 250/336.1

FOREIGN PATENT DOCUMENTS

| EP | 0 809 123 A2 | 11/1997 | |
| JP | 04265055 A * | 9/1992 | ................. 379/37 |
| WO | WO 99/21148 | 4/1999 | |

OTHER PUBLICATIONS

Xin-Zhong, Chen et al., "The Physics of Anti-Terrorist Safety Inspection Technology", Wuli Chinese Physics Soc. China, vol. 31, No. 9, Sep. 1, 2002, pp. 584-588, 10 pgs. of translation.

* cited by examiner

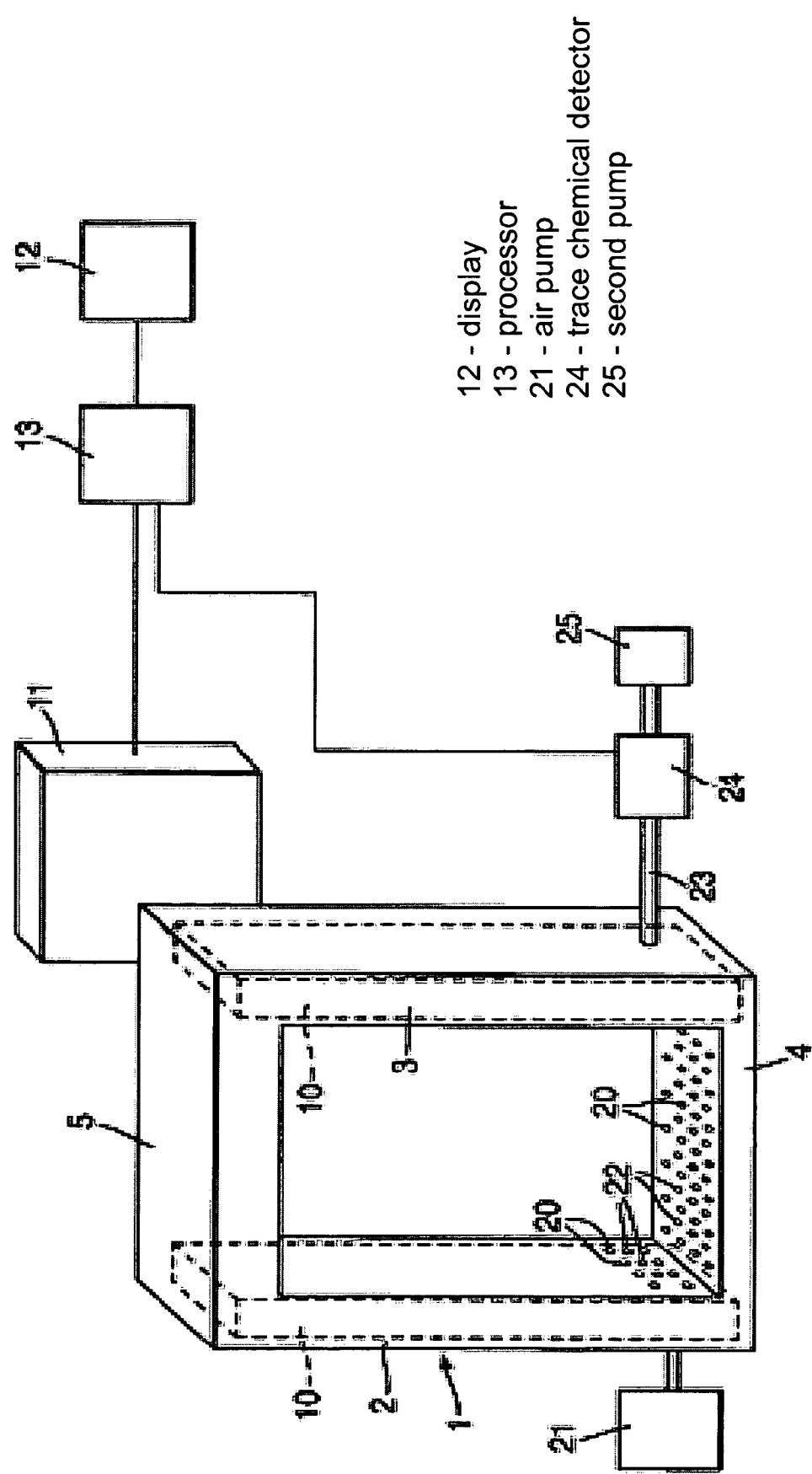

MILLIMETRE-WAVE DETECTION DEVICE FOR DISCRIMINATING BETWEEN DIFFERENT MATERIALS

CROSS-REFERENCE TO RELATED APPLICATIONS

This application claims benefit of Great Britain application 0321754.4, filed Sep. 17, 2003, including the specification, drawings, claims and abstract, which is incorporated herein by reference in its entirety. This application is a U.S. National Stage of Application PCT/GB2004/003902, filed Sep. 13, 2004, incorporated herein by reference in its entirety.

BACKGROUND

This invention relates to apparatus for detecting articles and substances concealed on a person.

Various techniques are used to detect concealed articles and substances on people, such as at airports. One familiar technique is the walk-through metal detector presently used at all major airports to detect concealed metal articles, such as guns or knives, carried by passengers. These work effectively and cause little delay but suffer from the disadvantage that they are unable to detect non-metal objects such as ceramic knives, explosives or narcotics. Another form of equipment in present use, but on a much smaller scale, is the trace chemical detector. In one form this is incorporated into a walk-through portal having multiple air jets directed over the body of the passenger and having suction inlets located to collect trace chemicals dislodged by the air jets. The collected air and trace chemicals is supplied to a chemical detector, which may take various different forms but typically might include an ion mobility spectrometer (IMS) arranged to respond to the presence of selected chemicals. Trace chemical detectors are available from Smiths Detection. Although trace chemical detectors can work effectively, they are relatively expensive and the response time is slower than metal detectors. Furthermore, they cannot detect knives or the like.

A further form of equipment has been proposed, but has not yet been used extensively, namely millimeter wave imaging. This uses radiation in the range of about 10 GHz to 400 GHz, usually around 93 GHz, which passes substantially unimpeded through clothing and thereby enables articles concealed beneath clothing to be detected. There are different techniques employing millimeter waves, such as described in U.S. Pat. No. 4,901,084, which employs polarized coherent radiation, or as described in U.S. Pat. No. 6,353,224, which employs a source of incoherent radiation intended to replicate normal background radiation in the open air. The advantage of millimeter wave imaging is that it can detect non-metal objects such as ceramic knives and explosives carried beneath clothing. The problem with millimeter wave imaging is that the radiation does not penetrate most shoes and boots. Also it can be difficult to detect thin sheets of explosives.

BRIEF SUMMARY

It is an object of the present invention to provide alternative apparatus for detecting articles concealed on the person.

According to the present invention there is provided apparatus of the above-specified kind, characterised in that the apparatus includes the combination of a millimeter wave detection device and a trace chemical detection device.

BRIEF DESCRIPTION OF THE DRAWING

FIG. 1 shows a portal having a one or more millimeter wavelength radiation sources and trace chemical detector.

DETAILED DESCRIPTION

The millimeter wave detection device is preferably responsive to substantially the entire body of the person and may be arranged to provide an image of the person. The trace chemical detection device is preferably arranged to detect trace chemicals only from a restricted part of the body. Preferably the trace chemical detection device is arranged to detect trace chemicals in the region of the feet of the person and may include an outlet arranged to direct a jet of air onto the feet of the person. The trace chemical detection device may include an ion mobility spectrometer and may be arranged to detect the presence of at least one of explosives and narcotics. The apparatus may include a plurality of millimetric wave detection devices and a trace chemical detection device common to the plurality of millimetric wave detection devices. The apparatus is preferably incorporated into one or more portals.

Apparatus for screening people, according to the present invention, will now be described, by way of example, with reference to the accompanying drawing which shows the apparatus schematically.

The apparatus employs a combination of two different techniques for detecting concealed materials and which complement one another because one technique is better able to detect materials in certain situations than the other. In particular, one technique employs millimetric wave detection and the other technique employs trace chemical detection.

The drawing shows a portal 1 having two vertical posts 2 and 3, a threshold 4 extending between the posts at floor level and a lintel 5 extending between the upper end of the posts. The dimensions of the portal 1 are such as to allow people to walk freely through between the posts. The portal 1 houses one or more millimeter wavelength radiation sources indicated generally by the numeral 10, such as of the kind described in U.S. Pat. No. 6,353,224. The sources 10 emit incoherent millimetric radiation and may include reflectors arranged to direct the radiation as necessary. The sources are arranged to illuminate substantially the entire body of the person walking through the portal 1 with the radiation. Mounted opposite the portal 1 is a millimetric wave detection device or imager 11 located to view the person being screened. The imager 11 may be mounted directly in front of the portal or to one side. There may be a second imager (not shown) arranged to view the rear of the person being screened. The imager 11 may be of the same kind as described in U.S. Pat. No. 6,353,224 and provides an output to a display 12 via a processor 13. The processor 13 is preferably arranged to generate a simulated image of the person's body and to superimpose on this representations of articles concealed beneath clothing. The processor may be arranged automatically to identify an article having a known characteristic typical of a weapon and, in this respect, it may not be necessary for the millimetric wave detection device to provide an image.

The portal also includes multiple air jet outlets 20 located towards the lower end of the posts 2 and 3 over a distance of about 50 cm. The outlets 20 are oriented to direct air jets horizontally, or at an angle downwardly, onto the feet and legs of the person being screened. There are also a number of air jet outlets 20 distributed over the upper surface of the threshold 4 to direct air jets upwardly. The outlets are connected to an air pump 21, which may include a filter for removing particles or environmental chemicals that could interfere with detection. The jets of air from the outlets 20 blow off particles of chemicals on the feet and the lower part of the legs of the person being screened. In addition to the air outlets 20, the portal 1 supports several air inlets 22 located in the same lower part of the portal. The inlets 22 connect via tubing 23 with a trace chemical detector 24 and a second pump 25. The detector 24 may be of a conventional kind and preferably includes an ion mobility spectrometer arranged to detect the presence of chemicals present in a number of different explosives and narcotics. The detector 24 also provides an output to the processor 13. When a suspect chemical is detected the processor 13 generates an alarm signal on the display 12. Generally, the alarm would simply indicate the presence of a suspect chemical somewhere on the lower part of the body of the person being screened. Alternatively, the detector 24 could have a number of different channels connected with air inlets 22 in different parts of the portal so that an indication could be given of the part of the body on which the chemical is concealed. The channels could be sampled sequentially by a single detector or each channel could have its own dedicated detector.

The arrangement described helps alleviate the difficulty that conventional millimetric wave imaging has detecting articles concealed in footwear by providing detection of trace chemicals in the region of the feet. Because the trace chemical detection system is confined to only a small part of the body it need only handle lower volumes of air enabling the system to be simplified, its cost to be reduced and its response time to be increased. It might be possible for a system of several portals to share a common IMS detection system because of the reduced volumes of air. The common IMS detection system could sample different portals sequentially. Alternatively, the portals could be sampled together and a warning provided if a suspect chemical was detected at any portal. A hand-held chemical trace detector could then be used to check the people at each portal.

Although there are advantages in confining the trace chemical detection to the foot region it would be possible to combine millimetric wave imaging with trace chemical detection from the entire body in order to improve the ability of the apparatus to detect articles having certain chemical compositions, such as explosives or narcotics, which are more difficult to detect, especially if formed into thin sheets. The combination of the techniques of millimetric wave imaging and trace chemical detection is particularly effective in detecting a wide range of potential threats. Combining the two techniques together in a single portal also helps reduce delay caused to people being screened compared with arrangements where people have to be screened separately by different techniques. The arrangement of the present invention can also reduce the workload on operators or enable the number of operators to be reduced.

The invention claimed is:

1. An apparatus for detecting articles and substances concealed on a person comprising a millimeter wave detection device and a trace chemical detector device;
   wherein the trace chemical detection device is arranged to detect trace chemicals from the region of the feet of the person.

2. The apparatus according to claim 1, wherein the millimetric wave detection device is responsive to substantially the entire body of the person.

3. The apparatus according to claim 1, wherein the millimetric wave detection device is arranged to provide an image of the person.

4. The apparatus according to claim 1, wherein the trace chemical detection device comprises an outlet arranged to direct a jet of air onto the feet of the person.

5. The apparatus according to claim 1, wherein the trace chemical detection device comprises an ion mobility spectrometer.

6. The apparatus according to claim 1, wherein the trace chemical detection device is arranged to detect the presence of at least one of explosives and narcotics.

7. The apparatus according to claim 1, wherein the apparatus comprises a plurality of millimetric wave detection devices and a trace chemical detection device common to the plurality of millimetric wave detection devices.

8. The apparatus according to claim 1, wherein the apparatus is incorporated into one or more portals.

* * * * *